(12) United States Patent
Lee

(10) Patent No.: US 6,913,887 B2
(45) Date of Patent: Jul. 5, 2005

(54) METHOD FOR DETECTING HEPATITIS C VIRUS

(75) Inventor: Tzong Hae Lee, San Francisco, CA (US)

(73) Assignee: Qgene Biotechnology, Inc., Kaohsiung (TW)

( * ) Notice: Subject to any disclaimer, the term of this patent is extended or adjusted under 35 U.S.C. 154(b) by 26 days.

(21) Appl. No.: 10/307,523

(22) Filed: Dec. 2, 2002

(65) Prior Publication Data

US 2004/0106099 A1 Jun. 3, 2004

(51) Int. Cl.$^7$ .......................... C12Q 1/68; C12P 19/34; C07H 21/00; C07H 21/02; C07H 21/04
(52) U.S. Cl. .................. 435/6; 435/91.1; 435/91.2; 536/23.1; 536/24.3; 536/25.3; 536/26.6
(58) Field of Search .................... 435/6, 91.1, 91.2; 536/23.1, 24.3, 25.3, 26.6

(56) References Cited

U.S. PATENT DOCUMENTS

2003/0124512 A1 * 7/2003 Stuyver ..................... 435/5
2004/0024193 A1 * 2/2004 Williams ................ 536/23.72

* cited by examiner

*Primary Examiner*—Jezia Riley
(74) *Attorney, Agent, or Firm*—Stevens, Davis, Miller, Mosher, LLP

(57) ABSTRACT

A method for detecting hepatitis C virus (HCV) in a sample includes the steps of (a) extracting RNA from the sample; (b) contacting the RNA to a reverse transcriptase and a downstream primer specific to the HCV RNA sequence to create cDNA; (c) forming an amplification medium by mixing the cDNA with a PCR reaction mixture, a nucleic-acid-binding fluorescent entity, and the downstream primer and an upstream primer specific to the HCV RNA sequence; (d) thermally cycling the amplification medium between at least a denaturation temperature and an elongation temperature; (e) illuminating the amplification medium with a selected wavelength of light that is absorbed by the fluorescent entity during the thermally cycling step; (f) determining the amount of fluorescence generated by the fluorescent entity; and (g) detecting the presence of the target nucleic acid by analyzing the amount of luminescence determined after at least one amplification cycle.

12 Claims, No Drawings

METHOD FOR DETECTING HEPATITIS C VIRUS

BACKGROUND OF THE INVENTION

1. Field of the Invention

This invention relates to a method for detecting or quantifying hepatitis C virus (HCV) in a sample.

2. Description of the Related Art

Hepatitis C virus (HCV) is a major cause of acute hepatitis and chronic liver disease, including cirrhosis and liver cancer. It has been estimated by the World Health Organization (WHO) that 170 million persons are chronically infected with HCV and 3 to 4 million persons are newly infected each year.

As is well known, hepatitis C virus is a small RNA virus containing a single, positive sense, molecule of RNA about 10,000 nucleotides in length. The cloning and sequencing of the HCV genome by Choo et al. (1989) has allowed the development of methods for detecting HCV infection via amplification of HCV RNA sequences by reverse transcription and cDNA polymerase chain reaction (RT-PCR) using primers derived from the HCV genomic sequence. However, traditional PCR methods do not allow accurate quantitation as the product is monitored beyond the exponential phase of PCR reaction and require laborious post-PCR processing. Moreover, methods such as enzyme immunosorbant assays (EIA) for the detection of HCV specific antibodies are not quantitative enough to reliably monitor decrease in viral reduction during antiviral therapy.

Accordingly, there exists a need in the art for a rapid and sensitive method for detecting or quantifying HCV in a sample.

SUMMARY OF THE INVENTION

It is an object of the present invention to develop a real-time PCR assay for directly detecting or quantifying Hepatitis C virus (HCV) in a sample in which detection steps are minimized resulting in a method which may be performed quickly, accurately and easily with minimal operator skill.

The inventors have developed a real-time PCR for the detection of HCV in a sample. One embodiment of the invention is directed to a method comprising the steps of: (a) extracting RNA from the sample; (b) contacting the RNA to a reverse transcriptase and a downstream primer having a nucleotide sequence substantially complementary to the HCV RNA sequence to create cDNA; (c) forming an amplification medium by mixing the cDNA with a thermostable polymerase, appropriate nucleoside triphosphates, a nucleic-acid-binding fluorescent entity, and the downstream primer and an upstream primer having a nucleotide sequence substantially complementary to the complement of the HCV RNA; (d) thermally cycling the amplification medium between at least a denaturation temperature and an elongation temperature, wherein the upstream and downstream primers in combination amplify a target nucleic acid; (e) illuminating the amplification medium with a selected wavelength of light that is absorbed by the fluorescent entity during the thermally cycling step; (f) determining the amount of fluorescence generated by the fluorescent entity; and (g) detecting the presence of the target nucleic acid by analyzing the amount of luminescence determined after at least one amplification cycle. As the target nucleic acid is an amplified product using two primers specific to the HCV RNA sequence, this method can be used to detect HCV in a sample, thus potentially providing information as to the likelihood of the sample donor suffering from the symptoms caused by the virus.

In another embodiment of the invention, a method for quantifying HCV in a sample is provided. This method is based on the fact that the amount of fluorescence is related to the amount of the target nucleic acid in the sample. Specifically, this method involves (a) determining a threshold cycle number at which the amount of fluorescence generated by the fluorescent entity in a sample reaches a fixed threshold value above a baseline value; and (b) calculating the quantity of the target nucleic acid in the sample by comparing the threshold cycle number determined for the target nucleic acid in a sample with the threshold cycle number determined for target nucleic acid of known amounts in standard solutions.

In the methods of the present invention, nucleic-acid-binding fluorescent entity, e.g., a double strand specific nucleic acid binding dye or a fluorescently labeled oligonucleotide probe, is used for the detection and analysis of the amplified product without the need for any subsequent handling step, thereby allowing a high-through-put method for directly detecting and quantifying HCV in a sample.

Preferably, after the aforementioned method is performed, the amount of fluorescence generated by the fluorescent entity is measured as a function of temperature to determine the melting profile of the amplified target nucleic acid. Thereafter, the amplified target nucleic acid can be characterized by analysis of the melting profile for confirmation of PCR specificity.

Other objects, advantages, and novel features of the invention will become more apparent from the following detailed description.

DETAILED DESCRIPTION OF THE PREFERRED EMBODIMENT

The present invention provides methods for detecting and quantifying the occurrence of hepatitis C virus (HCV) in samples. For example, methods of the invention may be used to detect and/or quantify the number of viral genomes present in a sample, quantitative methods being preferred. Methods according to the invention rely on amplifying a target nucleic acid using two primers specific to HCV RNA sequence in a real-time PCR method. The nucleotide sequence of the HCV genome identified from a cDNA clone was reported in Choo et al., 1991, Proc. Natl. Acad. Sci. USA 88:2451–2455, incorporated herein by reference. However, the genome of HCV exhibits a large degree of nucleic acid sequence heterogeneity among strains and isolates (see Simmonds, 1995, Hepatology 21:570–583, and Bukh et al., 1994, Proc. Natl. Acad. Sci. USA 91:8239–8243, both incorporated herein by reference). Because of the sequence heterogeneity among HCV strains, primers and probes are likely to be strain-specific, unless a region in which the sequence is conserved across strains can be found. One such conserved region is at the 5'-noncoding (5' NC) region of the HCV genome. Therefore, the target nucleic acid of the present invention preferably has the sequence found in the 5' NC region of the HCV genome. For example, a suitable target nucleic acid that is amplified in methods of the invention has the sequence shown in SEQ ID NO:1 or a section of it. Where the target sequence is a section of the sequence of SEQ ID NO:1, the section may be of any length provided that the section is unique to the HCV genome. For example, a section may comprise up to 50, up to 100 or up to 245 of the nucleotides of SEQ ID NO:1. Methods of the invention can detect and/or quantify HCV in samples taken from patients infected with HCV. Also, methods of the invention can be used to evaluate the effectiveness of antiviral drugs. In this case, cell cultures comprising HCV can be assayed using methods of the invention, the resulting information being used to determine what concentration of antiviral agent to use.

According to one embodiment of the present invention, a high-through-put method for directly detecting HCV in a biological sample (such as serum collected from humans infected with hepatitis C virus) is provided. First, the RNA to be analyzed can be isolated from the biological sample by methods known to those skilled in the art. A preferred method is extraction of RNA by silica-gel-membrane technologies developed by QIAGEN®. Then, the RNA can be reverse transcribed by a reverse transcriptase to first strand cDNA using a downstream primer nucleotide sequence substantially complementary to the nucleotide sequence of the HCV genome, i.e., the HCV RNA sequence. Once the cDNA are synthesized, a real-time PCR is carried out using the downstream primer and an upstream primer having a nucleotide sequence substantially complementary to the complement of the HCV RNA. Also, it is understood by those skilled in the art that the downstream primer is complementary to the original viral RNA and the upstream primer is complementary to the first strand of cDNA generated by reverse transcription of the viral RNA.

It is preferred that the downstream primer and upstream primers have nucleotide sequences substantially complementary to the sequence shown in SEQ ID NO:1 or the complement thereof, in the sense that every nucleotide will base pair with the one with which it pairs most stably (A with T or U; C with G). Preferred primers of the invention are the primers of SEQ ID NO:2 and SEQ ID NO:3. Preferably, the primers of the invention will be in isolated form, for example in aqueous solution.

Specifically, the real-time PCR is conducted by mixing the cDNA with a thermostable polymerase, appropriate nucleoside triphosphates, a nucleic-acid-binding fluorescent entity, and the downstream primer and upstream primers to create an amplification medium. The term "nucleoside triphosphate" is used herein to refer to nucleosides present in either DNA or RNA and thus includes nucleosides which incorporate adenine, cytosine, guanine, thymine and uracil as base, the sugar moiety being deoxyribose or ribose.

Suitable nucleic-acid-binding fluorescent entity for detecting and monitoring DNA amplification include double strand specific nucleic acid binding dyes or fluorescently labeled oligonucleotide probes. Those skilled in the art will be familiar with the use of ethidium bromide in monitoring DNA amplification. When a double strand-specific fluorescent dye is present during amplification, fluorescence generally increases as more double stranded product is made. It is preferred that SYBR® Green I, which is well known in the art and available from Molecular Probes of Eugene, Oreg., be used as a double-strand-specific dye. The molecular structure of this dye is a trade secret, but it is recommended by the manufacturer as a more sensitive double-strand-specific dye for DNA detection. A suitable fluorescently labeled probe is an oligonucleotide with both a reporter fluorescent dye and a quencher dye attached. While the probe is intact, the proximity of the quencher greatly reduces the fluorescence emitted by the reporter dye by Forster resonance energy transfer (FRET) through space.

Thereafter, the amplification medium is placed in a thermocycler for performing a thermally cycling reaction between at least a denaturation temperature and an elongation temperature. Any number of amplification cycles that amplifies the target sequence to a sufficient degree may be used wherein 45 to 50 cycles is particularly preferred. The amplification medium is irradiated with a selected wavelength of light and the resulting fluorescence is detected using a CCD array to capture an image of all samples. Fluorescence values are recorded during every thermal cycle and represent the amount of product amplified to that point in the amplification reaction. Software built in the thermocycler collects the images throughout the thermal cycling of PCR and analyzes the data to generate an amplification plot for each sample by plotting fluorescence signal versus cycle number.

Finally, analysis of the products of the amplification reaction is then carried out. Quantitative analyses are preferred, though detection of the target nucleic acid without quantification is also within the scope of the invention. Typically, the more template containing the target nucleic acid present at the beginning of the amplification reaction, the fewer number of cycles it takes to reach a point in which the fluorescent signal is first recorded as statistically significant above background. This point is defined as the $C_T$ (threshold cycle), and will always occur during the exponential phase of amplification. Since the amplified product of the target nucleic acid is only synthesized if the sample contains the target nucleic acid, the presence of the target nucleic acid can easily analyzed by determining if the calculated $C_T$ of a sample reaction is above a predetermined value. As the target nucleic acid is an amplified product using two primers specific to the HCV RNA sequence, the aforementioned method can be used to detect HCV in a sample, thus potentially providing information as to the likelihood of the sample donor suffering from the symptoms caused by the virus.

In another embodiment of the invention, a method for quantifying HCV in a sample is provided. In this embodiment, quantitation of target nucleic acid in unknown samples is accomplished by measuring $C_T$ and using a standard curve to determine the starting copy number. Specifically, this method involves (a) determining a $C_T$ at which the amount of fluorescence generated by the fluorescent entity in a sample reaches a fixed threshold value above a baseline value; and (b) calculating the quantity of the target nucleic acid in the sample by comparing the $C_T$ determined for the target nucleic acid in a sample with the $C_T$ determined for target nucleic acid of known amounts in standard solutions.

Preferably, DNA melting curves for different PCR products are acquired by fluorescence monitoring with double-strand-specific DNA specific dyes. Fluorescence data for melting curves is acquired by integrating the signal over 0.25–2.0 seconds during a linear temperature transition to 95° C. at 0.1–10° C./second. The fluorescence was continuously acquired and displayed at fluorescence versus temperature plots by software built in the thermocycler. As a PCR product is heated from the extension temperature to the denaturation temperature, any DNA in the sample is melted to single strands. This denaturation can be observed as a drop in the fluorescence of double-strand-specific DNA specific dye. Melting curve analysis can be used to differentiate intended product from nonspecific products such as primer dimers. Primer dimers melt over a wide range of low temperatures; very different from the sharp melting curves of specific PCR amplification products. Larger heterogeneous products have lower and broader melting curves when compared with pure PCR product. Therefore, the PCR products can be characterized by analysis of the melting profile thereof for confirmation of PCR specificity.

The invention is more particularly described by way of examples, which should not be construed as limiting the invention thereto.

EXAMPLE 1

Real-Time Monitoring of RT-PCR Amplification of HCV

RNA was extracted from serum by silica-gel-membrane technologies developed by QIAGEN® and the final RNA solution was stored at −70° C.

Then, RT-reaction mixture was prepared using concentrated stock solutions. The RT-reaction mixture consisted of the following:

| Reagents | Final Conc. |
| --- | --- |
| Buffer | 1× |
| Rnase inhibitor | 1 unit/µl |
| MuLV reverse transcriptase | 2.5 unit/µl |
| KY78 (SEQ ID NO: 2) | 0.75 µM |
| dNTPs | 100 mM each |
| Mg++ | 5 mM |

15 µl of the final RNA solution was used for cDNA synthesis that was performed in 5.11 µl of the RT-reaction mixture.

Thereafter, PCR-reaction mixture was prepared using concentrated stock solutions. The PCR-reaction mixture consisted of the following:

| Reagents | Final Conc. |
| --- | --- |
| PCR buffer | 1× |
| KY78 (SEQ ID NO: 2) | 0.3 µM |
| KY80 (SEQ ID NO: 3) | 0.3 µM |
| dNTPs | 100 mM each |
| SYBR ® Green I | 3.75× |
| Thermostable Polymerase | 0.7 unit/µl |

Then, 10 µl of the PCR-reaction mixture was aliquoted per reaction tube and 5 µl of resulting cDNA solution was added. In addition, 10 µl mineral oil per individual tube was added. It is preferred that HCV Optimal Buffer™ which contains water, tris, triston, MgCl, KCl and BSA, and is available from QGENE Biotechnology Inc. be used as a PCR buffer. In addition, thermal stable DNA polymerases which activate upon heating to high temperatures (e.g., above 60° C.) may be used. Suitable thermal stable DNA polymerases include the ones described in Roche U.S. Pat. No. 5,677,152. Cycling was performed in GeneAmp® 5700 Sequence Detection System and the following cycling conditions were used:

| | | |
| --- | --- | --- |
| 95° C.: | 10 min | (1×) |
| 95° C.: | 30 sec | (50×) |
| 64° C.: | 30 sec | (50×) |
| 72° C.: | 45 sec | (50×) |

The $C_T$ value is 50 when samples from HCV-negative patients were used as templates. The $C_T$ values were less than 40 when samples from patients with HCV infection were used as templates.

EXAMPLE 2

Quantitative Measurements Using Real-Time Monitoring of HCV

Then, 5.11 µl of the RT-reaction mixture was aliquoted per reaction tube and 15 µl of synthetic HCV RNA template (different dilutions of a stock) was added to obtain cDNA having a nucleotide sequence complementary to the sequence shown in SEQ ID NO:1. Then, 10 µl of the PCR-reaction mixture was aliquoted per reaction tube and 5 µl of cDNA solution of standard was added. In addition, 10 µl mineral oil per individual tube was added. Thereafter, a standard curve is generated by plotting the CT values, with 95% confidence intervals, against the logarithm of the initial copy numbers. Accordingly, quantitation of the amount of target nucleic acid in unknown samples is accomplished by measuring CT and using the standard curve to determine the starting copy number.

Although the invention has been explained in relation to its preferred embodiment, it is to be understood that many other possible modifications and variations can be made without departing from the spirit and scope of the invention as hereinafter claimed.

Sequence Information

Target Sequence

```
245 bp Target Sequence
GCAGAAAGCG TCTAGCCATG GCGTTAGTAT GAGTGTCGTA CAGCCTCCAG  SEQ ID NO:1

GCCCCCCCCT CCCGGGAGAG CCATAGTGGT CTGCGGAACC GGTGAGTACA

CCGGAATTAC CGGAAAGACT GGGTCCTTTC TTGGATAAAC CCACTCTGTG

TCCGGTCATT TGGGCGTGCC CCCGCAAGAC TGCTAGCCGA GTAGCGTTGG

GTTGCGAAAG GCCTTGTGGT ACTGCCTGAT AGGGTGCTTG CGAGT
```

Primers

KY78

5' CTC GCA AGC ACC CTA TCA GGC AGT 3'  (SEQ ID NO:2)

KY80

5' GCA GAA AGC GTC TAG CCA TGG CGT 3'  (SEQ ID NO:3)

What is claimed is:

1. A method for detecting the hepatitis C virus (HCV) in a sample, the method comprising the steps of:
   (a) extracting RNA from the sample;
   (b) contacting the RNA to a reverse transcriptase and a downstream primer having a nucleotide sequence substantially complementary to the HCV RNA sequence to create cDNA;
   (c) forming an amplification medium by mixing the cDNA with a thermostable polymerase, appropriate nucleoside triphosphates, a nucleic-acid-binding fluorescent entity, and the downstream primer and an, upstream primer having a nucleotide sequence substantially complementary to a target nucleic acid having the sequence represented by SEQ ID NO:1 or the complement thereof;
   (d) thermally cycling the amplification medium between at least a denaturation temperature and an elongation temperature, wherein the upstream and downstream primers in combination amplify the target nucleic acid represented by SEQ ID NO:1, or a section thereof, wherein where the target sequence is said section of the sequence of SEQ ID NO:1, the section may be of any length provided that the section is unique to the HCV genome;
   (e) illuminating the amplification medium with a selected wavelength of light that is absorbed by the fluorescent entity during the thermally cycling step;
   (f) determining the amount of fluorescence generated by the fluorescent entity; and
   (g) detecting the presence of the target nucleic acid by analyzing the amount of luminescence determined after at least one amplification cycle.

2. The method as claimed in claim 1, wherein the method is used to determine the quantity of the HCV RNA in a sample, the method further comprises:
   (h) determining a threshold cycle number at which the amount of fluorescence generated by the fluorescent entity in a sample reaches a fixed threshold value above a baseline value; and
   (i) calculating the quantity of the HCV RNA in the sample by comparing the threshold cycle number determined for the target nucleic acid in the sample with the threshold cycle number determined for target nucleic acid of known amounts in standard solutions.

3. The method as claimed in claim 1, wherein the fluorescent entity comprises a double strand specific nucleic acid binding dye.

4. The method as claimed in claim 3, further comprising the step of:
   (h) measuring the amount of fluorescence as a function of temperature to determine the melting profile of the target nucleic acid; and characterizing the target nucleic acid by analysis of the melting profile.

5. The method as claimed in claim 1, wherein the fluorescent entity comprises a fluorescently labeled oligonucleotide probe that hybridizes to the target nucleic acid or the complement of the target nucleic acid.

6. The method as claimed in claim 1, wherein the RNA of step b, contacted to the reverse transcriptase and the downstream primer, consists essentially of RNA from serum of a person.

7. The method as claimed in claim 1, wherein at least one primer is the nucleic acid molecule of SEQ ID NO:2.

8. The method as claimed in claim 1, wherein at least one primer is the nucleic acid molecule of SEQ ID NO:3.

9. The method as claimed in claim 1, wherein one primer is the nucleic acid molecule of SEQ ID NO:2 and the other primer is the nucleic acid molecule of SEQ ID NO:3.

10. A kit for detection of the hepatitis C virus (HCV) in a sample, the kit comprising: a nucleic acid having the sequence shown in SEQ ID NO:1; and a pair of primers that have nucleotide sequences substantially complementary to the nucleic acid or the complement of the nucleic acid.

11. The kit as claimed in claim 9, wherein one primer is the nucleic acid molecule of SEQ ID NO:2 and the other primer is the nucleic acid molecule of SEQ ID NO:3.

12. A nucleic acid molecule selected from the group consisting of:

```
CTC GCA AGC ACC CTA TCA GGC AGT     (SEQ ID NO:2)

and

GCA GAA AGC GTC TAG CCA TGG CGT     (SEQ ID NO:3).
```

* * * * *

SEQUENCE LISTING

<160> NUMBER OF SEQ ID NOS: 3

<210> SEQ ID NO 1
<211> LENGTH: 245
<212> TYPE: DNA
<213> ORGANISM: Hepatitis C virus

<400> SEQUENCE: 1

```
gcagaaagcg tctagccatg gcgttagtat gagtgtcgta cagcctccag gcccccccct      60
cccgggagag ccatagtggt ctgcggaacc ggtgagtaca ccggaattac cggaaagact     120
gggtcctttc ttggataaac ccactctgtg tccggtcatt tgggcgtgcc cccgcaagac     180
tgctagccga gtagcgttgg gttgcgaaag gccttgtggt actgcctgat agggtgcttg     240
cgagt                                                                 245
```

<210> SEQ ID NO 2
<211> LENGTH: 24
<212> TYPE: DNA
<213> ORGANISM: Artificial
<220> FEATURE:
<223> OTHER INFORMATION: SYNTHETIC

<400> SEQUENCE: 2

```
ctcgcaagca ccctatcagg cagt                                             24
```

<210> SEQ ID NO 3
<211> LENGTH: 24
<212> TYPE: DNA
<213> ORGANISM: Artificial
<220> FEATURE:
<223> OTHER INFORMATION: SYNTHETIC

<400> SEQUENCE: 3

```
gcagaaagcg tctagccatg gcgt                                             24
```